United States Patent
Froehler et al.

(10) Patent No.: US 6,495,672 B1
(45) Date of Patent: Dec. 17, 2002

(54) OLIGONUCLEOTIDES INCLUDING 2-AMINOPYRIDINE AND 2-PYRIDONE C-NUCLEOSIDE UNITS

(75) Inventors: Brian C. Froehler, Belmont; Arnold J. Gutierrez, San Jose; Mark D. Matteucci, Portola Valley, all of CA (US)

(73) Assignee: ISIS Pharmaceuticals, Inc., Carlsbad, CA (US)

(*) Notice: Subject to any disclaimer, the term of this patent is extended or adjusted under 35 U.S.C. 154(b) by 0 days.

(21) Appl. No.: 09/717,422

(22) Filed: Nov. 21, 2000

Related U.S. Application Data

(62) Division of application No. 08/906,378, filed on Aug. 5, 1997.
(60) Provisional application No. 60/023,241, filed on Aug. 9, 1996.

(51) Int. Cl.$^7$ ................................................. C07H 21/00
(52) U.S. Cl. ...................... 536/23.1; 536/24.3; 536/24.5
(58) Field of Search .............................. 536/23.1, 24.3, 536/24.5

(56) References Cited

U.S. PATENT DOCUMENTS

| | | | | |
|---|---|---|---|---|
| 4,656,260 A | * | 4/1987 | Kato et al. | .................. 536/29.2 |
| 5,082,934 A | * | 1/1992 | Saba et al. | .................. 536/29.2 |
| 5,137,876 A | * | 8/1992 | MacCoss et al. | ............. 514/23 |

FOREIGN PATENT DOCUMENTS

WO            9741140       * 11/1997

OTHER PUBLICATIONS

Hsieh et al., "Syntheses of Two Pyridine C–Nucleosides as "Deletion–Modified" Analogues of dT and dC," *Journal of Organic Chemistry*, 60(16), 5356–5359 (Aug. 11, 1995).*
Bates et al., "Efficient Triple Helix Formation by Oligodeoxyribonucleotides Containing a–or β–2–Amino–5–(2–deoxy–D–ribofuranosyl)pyridine Residues," *Nucleic Acids Research*, 24(21), 4176–4184 (Nov. 1, 1996).*
Hildebrand et al.(I), "5–Substituted 2–Aminopyridine C–Nucleosides as Protonated Cytidine Equivalents: Increasing Efficiency and Selectivity in DNA Triple–Helix Formation," *Journal of the American Chemical Society*, 119(24), 5499–5511 (Jun. 18, 1997).*
Matulic–Adamic et al., "Synthesis of 5–(β–D–Ribofuranosyl)–pyridin–2–one: A 'Deletion–Modified' Analogue of Uridine," *Tetrahedron Letters*, 38(10), 1669–1672 (Mar. 10, 1997).*
Watanabe, "Equimolecular Reaction of Showdomycin with Thiols," *Journal of Antibiotics*, 23(6), 313–314 (Jun., 1970).*
Ohrui et al., "Nucleosides LXXXI. An Approach to the Synthesis of C–C Linked β–D–Ribofuranosyl Nucleosides from 2,3–O–Isopropylidene–5–O–trityl–β–D–ribofuranosyl Chloride," *Tetrahedron Letters*, (Issue No. 22), 1951–1954 (May, 1973).*
Schwartz et al., "Synthesis and Properties of N–(2, 3, 5–Tri–O–acetyl–D–ribofuranosyl)maleimide," *Journal of Organic Chemistry*, 40(1), 24–28 (Jan. 10, 1975).*
Hildebrand et al.(II), "Enhancing DNA Triple Helix Stability at Neutral pH By the Use of Oligonucleotides Containing a More Basic Deoxycytidine Analog," *Angewandte Chemie, Intl. Ed.,* 35(17), 1968–1970 (Sep. 20, 1996).*
Mertes et al., "Approaches to the Synthesis of 1–Deazauridine and 2'–Deoxy–1–deazauridine," *Journal of Medicinal Chemistry*, 10, 320–325 (May, 1967).*
Cooney et al., "Site–Specific Oligonucleotide Binding Represses Transcription of the Human c–myc Gene in Vitro", *Science*, Jul. 22, 1988, vol. 241, pp. 456–459.
Francois et al., "Sequence–Specific Recognition of the Magor Groove of DNA by Oligodeoxynucleotides Via Triple Helix Formation. Footprinting Studies", *Nucleic Acids Research*, Dec. 23, 1988, vol. 16, No. 24, pp. 11431–11440.
Froehler et al., "Triple–Helix Formation by Oligodeoxynucleotides Containing the Carbocyclic Analogues of Thymidine and 5–Methyl–2'–deoxycytidine", *Journal of the American Chemical Society*, Oct. 7, 1992, vol. 114, No. 21, pp. 8320–8322.
Matteucci et al., "Deoxyoligonucleotides Bearing Analogues of Posphosdiester Linkages Recognize Duplex DNA Via Triple–Helix Formation", *Journal of the American Chemical Society*, Sep. 25, 1991, vol. 113, No. 20, pp. 7767–7768.
Rajur et al., "The Synthesis of Oligodeoxynucleotides Containing 2–Thiothymidine and 5–Methyl–4–Pyrimidinone Base Ananlogues", *Tetrahedron Letters*, Oct. 6, 1992, vol. 33, No. 41, pp. 6081–6084.

* cited by examiner

Primary Examiner—Paul J. Killos
Assistant Examiner—Lawrence E. Crane
(74) Attorney, Agent, or Firm—Woodcock Washburn LLP

(57) ABSTRACT

The present invention provides 2-aminopyridine and 2-pyridone C-nucleosides and oligonucleotides containing the subject nucleosides. The nucleosides are useful in the preparation of the subject oligonucleotides. The oligonucleotides are useful in oligonucleotide-based diagnosis and separation through triplex binding.

2 Claims, No Drawings

SEQUENCE LISTING

<160> NUMBER OF SEQ ID NOS: 9

<210> SEQ ID NO 1
<211> LENGTH: 15
<212> TYPE: DNA
<213> ORGANISM: Artificial Sequence
<220> FEATURE:
<223> OTHER INFORMATION: Novel Sequence

<400> SEQUENCE: 1
tctccctctc ttttt                                                15

<210> SEQ ID NO 2
<211> LENGTH: 15
<212> TYPE: DNA
<213> ORGANISM: Artificial Sequence
<220> FEATURE:
<223> OTHER INFORMATION: Novel Sequence

<400> SEQUENCE: 2
tctctctctc ttttt                                                15

<210> SEQ ID NO 3
<211> LENGTH: 15
<212> TYPE: DNA
<213> ORGANISM: Artificial Sequence
<220> FEATURE:
<223> OTHER INFORMATION: Novel Sequence
<221> NAME/KEY: misc_feature
<222> LOCATION: (2)..(2)
<223> OTHER INFORMATION: N is 5-methyl dC
<221> NAME/KEY: misc_feature
<222> LOCATION: (4)..(4)
<223> OTHER INFORMATION: N is 5-methyl dC
<221> NAME/KEY: misc_feature
<222> LOCATION: (6)..(6)
<223> OTHER INFORMATION: N is 5-methyl dC
<221> NAME/KEY: misc_feature
<222> LOCATION: (8)..(8)
<223> OTHER INFORMATION: N is 5-methyl dC
<221> NAME/KEY: misc_feature
<222> LOCATION: (10)..(10)
<223> OTHER INFORMATION: N is 5-methyl dC

<400> SEQUENCE: 3
tntntntntn ttttt                                                15

<210> SEQ ID NO 4
<211> LENGTH: 15
<212> TYPE: DNA
<213> ORGANISM: Artificial Sequence
<220> FEATURE:
<223> OTHER INFORMATION: Novel Sequence
<221> NAME/KEY: misc_feature
<222> LOCATION: (2)..(2)
<223> OTHER INFORMATION: N is 2-aminopyridine
<221> NAME/KEY: misc_feature
<222> LOCATION: (4)..(4)
<223> OTHER INFORMATION: N is 2-aminopyridine
<221> NAME/KEY: misc_feature
<222> LOCATION: (6)..(6)
<223> OTHER INFORMATION: N is 2-aminopyridine
<221> NAME/KEY: misc_feature
<222> LOCATION: (8)..(8)
<223> OTHER INFORMATION: N is 2-aminopyridine
<221> NAME/KEY: misc_feature
<222> LOCATION: (10)..(10)
<223> OTHER INFORMATION: N is 2-aminopyridine

<400> SEQUENCE: 4
tntntntntn ttttt                                                                                  15

<210> SEQ ID NO 5
<211> LENGTH: 15
<212> TYPE: RNA
<213> ORGANISM: Artificial Sequence
<220> FEATURE:
<223> OTHER INFORMATION: Novel Sequence
<221> NAME/KEY: misc_feature
<222> LOCATION: (1)..(1)
<223> OTHER INFORMATION: N is 2-pyridinone
<221> NAME/KEY: misc_feature
<222> LOCATION: (2)..(2)
<223> OTHER INFORMATION: N is 2-aminopyridine
<221> NAME/KEY: misc_feature
<222> LOCATION: (3)..(3)
<223> OTHER INFORMATION: N is 2-pyridinone
<221> NAME/KEY: misc_feature
<222> LOCATION: (4)..(4)
<223> OTHER INFORMATION: N is 2-aminopyridine
<221> NAME/KEY: misc_feature
<222> LOCATION: (5)..(5)
<223> OTHER INFORMATION: N is 2-pyridinone
<221> NAME/KEY: misc_feature
<222> LOCATION: (6)..(6)
<223> OTHER INFORMATION: N is 2-aminopyridine
<221> NAME/KEY: misc_feature
<222> LOCATION: (7)..(7)
<223> OTHER INFORMATION: N is 2-pyridinone
<221> NAME/KEY: misc_feature
<222> LOCATION: (8)..(8)
<223> OTHER INFORMATION: N is 2-aminopyridine
<221> NAME/KEY: misc_feature
<222> LOCATION: (9)..(9)
<223> OTHER INFORMATION: N is 2-pyridinone
<221> NAME/KEY: misc_feature
<222> LOCATION: (10)..(10)
<223> OTHER INFORMATION: N is 2-aminopyridine
<221> NAME/KEY: misc_feature
<222> LOCATION: (11)..(15)
<223> OTHER INFORMATION: N is 2-pyridinone

<400> SEQUENCE: 5
nnnnnnnnnn nnnnn                                                                                  15

<210> SEQ ID NO 6
<211> LENGTH: 15
<212> TYPE: DNA
<213> ORGANISM: Artificial Sequence
<220> FEATURE:
<223> OTHER INFORMATION: Novel Sequence
<221> NAME/KEY: misc_feature
<222> LOCATION: (2)..(2)
<223> OTHER INFORMATION: N is 2-aminopyridine
<221> NAME/KEY: misc_feature
<222> LOCATION: (4)..(6)
<223> OTHER INFORMATION: N is 2-aminopyridine
<221> NAME/KEY: misc_feature
<222> LOCATION: (8)..(8)
<223> OTHER INFORMATION: N is 2-aminopyridine
<221> NAME/KEY: misc_feature
<222> LOCATION: (10)..(10)
<223> OTHER INFORMATION: N is 2-aminopyridine

<400> SEQUENCE: 6
tntnnntntn ttttt                                                                                  15

<210> SEQ ID NO 7
<211> LENGTH: 15
<212> TYPE: DNA
<213> ORGANISM: Artificial Sequence

```
<220> FEATURE:
<223> OTHER INFORMATION: Novel Sequence
<221> NAME/KEY: misc_feature
<222> LOCATION: (2)..(2)
<223> OTHER INFORMATION: N is 5-methyl dC
<221> NAME/KEY: misc_feature
<222> LOCATION: (4)..(4)
<223> OTHER INFORMATION: N is 5-methyl dC
<221> NAME/KEY: misc_feature
<222> LOCATION: (6)..(6)
<223> OTHER INFORMATION: N is 5-methyl dC
<221> NAME/KEY: misc_feature
<222> LOCATION: (8)..(8)
<223> OTHER INFORMATION: N is 5-methyl dC
<221> NAME/KEY: misc_feature
<222> LOCATION: (10)..(10)
<223> OTHER INFORMATION: N is 5-methyl dC

<400> SEQUENCE: 7
tntntntntn ttttt                                                    15

<210> SEQ ID NO 8
<211> LENGTH: 15
<212> TYPE: RNA
<213> ORGANISM: Artificial Sequence
<220> FEATURE:
<223> OTHER INFORMATION: Novel Sequence
<221> NAME/KEY: misc_feature
<222> LOCATION: (1)..(1)
<223> OTHER INFORMATION: N is 2-pyridinone
<221> NAME/KEY: misc_feature
<222> LOCATION: (2)..(2)
<223> OTHER INFORMATION: N is 2-aminopyridine
<221> NAME/KEY: misc_feature
<222> LOCATION: (3)..(3)
<223> OTHER INFORMATION: N is 2-pyridinone
<221> NAME/KEY: misc_feature
<222> LOCATION: (4)..(4)
<223> OTHER INFORMATION: N is 2-aminopyridine
<221> NAME/KEY: misc_feature
<222> LOCATION: (5)..(5)
<223> OTHER INFORMATION: N is 2-pyridinone
<221> NAME/KEY: misc_feature
<222> LOCATION: (6)..(6)
<223> OTHER INFORMATION: N is 2-aminopyridine
<221> NAME/KEY: misc_feature
<222> LOCATION: (7)..(7)
<223> OTHER INFORMATION: N is 2-pyridinone
<221> NAME/KEY: misc_feature
<222> LOCATION: (8)..(8)
<223> OTHER INFORMATION: N is 2-aminopyridine
<221> NAME/KEY: misc_feature
<222> LOCATION: (9)..(9)
<223> OTHER INFORMATION: N is 2-pyridinone
<221> NAME/KEY: misc_feature
<222> LOCATION: (10)..(10)
<223> OTHER INFORMATION: N is 2-aminopyridine
<221> NAME/KEY: misc_feature
<222> LOCATION: (11)..(15)
<223> OTHER INFORMATION: N is 2-pyridinone

<400> SEQUENCE: 8
nnnnnnnnnn nnnnn                                                    15

<210> SEQ ID NO 9
<211> LENGTH: 15
<212> TYPE: DNA
<213> ORGANISM: Artificial Sequence
<220> FEATURE:
<223> OTHER INFORMATION: Novel Sequence
<221> NAME/KEY: misc_feature
<222> LOCATION: (11)..(15)
<223> OTHER INFORMATION: N is 2-pyridinone
```

```
<400> SEQUENCE: 9
tctctctctc nnnnn                                              15
```

OLIGONUCLEOTIDES INCLUDING 2-AMINOPYRIDINE AND 2-PYRIDONE C-NUCLEOSIDE UNITS

CROSS REFERENCE TO RELATED APPLICATIONS

This patent application is a divisional of U.S. patent application Ser. No. 08/906,378, filed Aug. 5, 1997, which claims benefit of Provisional application Ser. No. 60/023,241, filed Aug. 9, 1996.

BACKGROUND OF THE INVENTION

1. Field of the Invention

The present invention is related to enhanced triplex binding and compositions useful in achieving enhanced triplex binding. In some embodiments, the invention provides modified nucleosides that provide enhanced triplex binding of single stranded oligonucleotides containing one or more of the modified nucleosides to target duplex oligonucleotides. Also provided by the invention are methods of using the modified nucleosides to prepare oligonucleotides containing them and methods of using the oligonucleotides containing the modified nucleosides in triplex binding assays and methods of separation.

2. Brief Description of Related Art

Hsieh, H.-P. and McLaughlin, L. W., *J. Org. Chem.* (1995), 60:5356–5359, discloses the syntheses of two pyridine C-nucleosides as "deletion-modified" analogues of dT and dC.

OBJECTS OF THE INVENTION

Selected embodiments of the present invention accomplish one or more of the following objects:

A principal object of the invention is sequence specific triplex binding of single stranded oligonucleotides to duplex oligonucleotides. In particular an object is diagnosis through triplex binding.

An additional object of the invention is to provide 2-aminopyridine and 2-pyridone C-nucleosides.

An additional object of the invention is to provide oligonucleotides containing 2-aminopyridine and 2-pyridone C-nucleosides.

An additional object of the invention is to provide 2-aminopyridine and 2-pyridone C-nucleosides as intermediates in the preparation of oligonucleotides containing 2-aminopyridine and 2-pyridone C-nucleosides.

SUMMARY OF THE INVENTION

Compounds or compositions having formula (I) or (II) are provided herein:

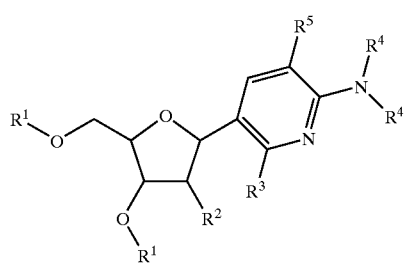

I

-continued
or

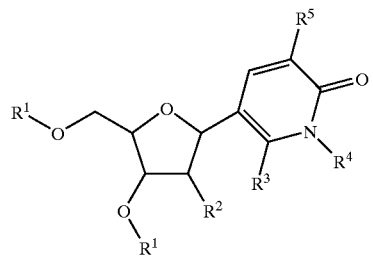

II wherein:
each $R^1$ is independently H or a hydroxy protecting group, or both $R^1$ groups are taken together to form a cyclic hydroxy protecting group;
$R^2$ is H, F, —$OR^1$, or —$OR^6$;
$R^3$ is H or —$CH_3$;
each $R^4$ of formula I and II is independently H or an amine protecting group, or both $R^4$ groups of formula I are taken together to form a cyclic amine protecting group;
$R^5$ is H, —$CH_3$ or —C≡C—$CH_3$; and
$R^6$ is

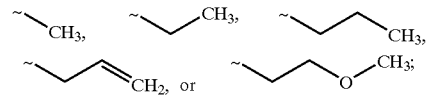

and salts, solvates, resolved enantiomers and purified diastereomers thereof.

Another aspect of the invention is directed to oligomers capable of triple helix formation comprising a multiplicity of nucleosides linked by internucleoside linkages wherein at least one nucleoside is a modified nucleoside comprising a nucleoside composition of the invention.

Another aspect of the invention is directed to methods of detecting the presence, absence or amount of a particular DNA duplex in a sample suspected of containing DNA comprising contacting the sample with an oligomer of the invention under conditions wherein a triple helix is formed between the oligomer and the particular DNA duplex.

DETAILED DESCRIPTION

The present invention is directed to 2-aminopyridine and 2-pyridone C-nucleosides. In particular the invention is directed to compositions comprising a compound of the formula:

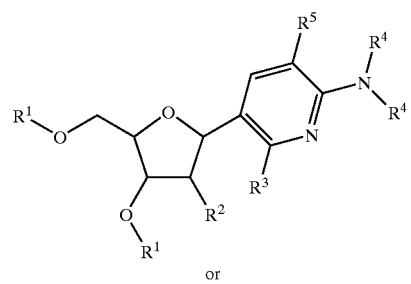

I or

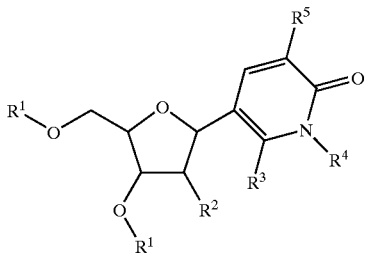

Each $R^1$ is independently H or a hydroxy protecting group, or both $R^1$ groups are taken together to form a cyclic hydroxy protecting group. Typically, each $R^1$ is H.

Typical $R^1$ hydroxy protecting groups described in Greene (pages 14–118) include Ethers (Methyl); Substituted Methyl Ethers (Methoxymethyl, Methylthiomethyl, t-Butylthiomethyl, (Phenyldimethylsilyl)methoxymethyl, Benzyloxymethyl, p-Methoxybenzyloxymethyl, (4-Methoxyphenoxy)methyl, Guaiacolmethyl, t-Butoxymethyl, 4-Pentenyloxymethyl, Siloxymethyl, 2-Methoxyethoxymethyl, 2,2,2-Trichloroethoxymethyl, Bis (2-chloroethoxy)methyl, 2-(Trimethylsilyl)ethoxymethyl, Tetrahydropyranyl, 3-Bromotetrahydropyranyl, Tetrahydropthiopyranyl, 1-Methoxycyclohexyl, 4-Methoxytetrahydropyranyl, 4-Methoxytetrahydrothiopyranyl, 4-Methoxytetrahydropthiopyranyl S,S-Dioxido, 1-[(2-Chloro-4-methyl)phenyl]-4-methoxypiperidin-4-yl, 35, 1,4-Dioxan-2-yl, Tetrahydrofuranyl, Tetrahydrothiofuranyl, 2,3,3a,4,5,6,7,7a-Octahydro-7,8,8-trimethyl-4,7-methanobenzofuran-2-yl)); Substituted Ethyl Ethers (1-Ethoxyethyl, 1-(2-Chloroethoxy)ethyl, 1-Methyl-1-methoxyethyl, 1-Methyl-1-benzyloxyethyl, 1-Methyl-1-benzyloxy-2-fluoroethyl, 2,2,2-Trichloroethyl, 2-Trimethylsilylethyl, 2-(Phenylselenyl)ethyl, t-Butyl, Allyl, p-Chlorophenyl, p-Methoxyphenyl, 2,4-Dinitrophenyl, Benzyl); Substituted Benzyl Ethers (p-Methoxybenzyl, 3,4-Dimethoxybenzyl, o-Nitrobenzyl, p-Nitrobenzyl, p-Halobenzyl, 2,6-Dichlorobenzyl, p-Cyanobenzyl, p-Phenylbenzyl, 2- and 4-Picolyl, 3-Methyl-2-picolyl N-Oxido, Diphenylmethyl, p,p'-Dinitrobenzhydryl, 5-Dibenzosuberyl, Triphenylmethyl, α-Naphthyldiphenylmethyl, p-methoxyphenyldiphenylmethyl, Di(p-methoxyphenyl) phenylmethyl, Tri(p-methoxyphenyl)methyl, 4-(4'-Bromophenacyloxy)phenyldiphenylmethyl, 4,4',-4"-Tris(-4,5-dichlorophthalimidophenyl)methyl, 4,4',4"-Tris (levulinoyloxyphenyl)methyl, 4,4',4"-Tris (benzoyloxyphenyl)methyl, 3-(Imidazol-1-ylmethyl)bis(4', 4"-dimethoxyphenyl)methyl, 1,1-Bis(4-methoxyphenyl)-1'-pyrenylmethyl, 9-Anthryl, 9-(9-Phenyl)xanthenyl, 9-(9-Phenyl-10-oxo)anthryl, 1,3-Benzodithiolan-2-yl, Benzisothiazolyl S,S-Dioxido); Silyl Ethers (Trimethylsilyl, Triethylsilyl, Triisopropylsilyl, Dimethylisopropylsilyl, Diethylisopropylsily, Dimethylthexylsilyl, t-Butyldimethylsilyl, t-Butyldiphenylsilyl, Tribenzylsilyl, Tri-p-xylylsilyl, Triphenylsilyl, Diphenylmethylsilyl, t-Butylmethoxyphenylsilyl); Esters (Formate, Benzoylformate, Acetate, Choroacetate, Dichloroacetate, Trichloroacetate, Trifluoroacetate, Methoxyacetate, Triphenylmethoxyacetate, Phenoxyacetate, p-Chlorophenoxyacetate, p-poly-Phenylacetate, 3-Phenylpropionate, 4-Oxopentanoate (Levulinate), 4,4-(Ethylenedithio)pentanoate, Pivaloate, Adamantoate, Crotonate, 4-Methoxycrotonate, Benzoate, p-Phenylbenzoate, 2,4,6-Trimethylbenzoate (Mesitoate)); Carbonates (Methyl, 9-Fluorenylmethyl, Ethyl, 2,2,2-Trichloroethyl, 2-(Trimethylsilyl)ethyl, 2-(Phenylsulfonyl) ethyl, 2-(Triphenylphosphonio)ethyl, Isobutyl, Vinyl, Allyl, p-Nitrophenyl, Benzyl, p-Methoxybenzyl, 3,4-Dimethoxybenzyl, o-Nitrobenzyl, p-Nitrobenzyl, S-Benzyl Thiocarbonate, 4-Ethoxy-1-naphthyl, Methyl Dithiocarbonate); Groups With Assisted Cleavage (2-Iodobenzoate, -4-Azidobutyrate, 4-Niotro-4-methylpentanoate, o-(Dibromomethyl)benzoate, 2-Formylbenzenesulfonate, 2-(Methylthiomethoxy)ethyl Carbonate, 4-(Methylthiomethoxy)butyrate, 2-(Methylthiomethoxymethyl)benzoate); Miscellaneous Esters (2,6-Dichloro-4-methylphenoxyacetate, 2,6-Dichloro-4-(1,1,3,3 tetramethylbutyl)phenoxyacetate, 2,4-Bis(1,1-dimethylpropyl)phenoxyacetate, Chorodiphenylacetate, Isobutyrate, Monosuccinoate, (E)-2-Methyl-2-butenoate (Tigloate), o-(Methoxycarbonyl) benzoate, p-poly-Benzoate, α-Naphthoate, Nitrate, Alkyl N,N,N',N'-Tetramethylphosphorodiamidate, N-Phenylcarbamate, Borate, Dimethylphosphinothioyl, 2,4-Dinitrophenylsulfenate); and Sulfonates (Sulfate, Methanesulfonate (Mesylate), Benzylsulfonate, Tosylate).

More typically, $R^1$ hydroxy protecting groups include substituted methyl ethers, substituted benzyl ethers, silyl ethers, and esters including sulfonic acid esters, still more typically, trialkylsilyl ethers, tosylates and acetates.

Typical 1,2-diol protecting groups (thus, generally where two OH groups are taken together with the $R^1$ protecting functionality) are described in Greene at pages 118–142 and include Cyclic Acetals and Ketals (Methylene, Ethylidene, 1-t-Butylethylidene, 1-Phenylethylidene, (4-Methoxyphenyl)ethylidene, 2,2,2-Trichloroethylidene, Acetonide (Isopropylidene), Cyclopentylidene, Cyclohexylidene, Cycloheptylidene, Benzylidene, p-Methoxybenzylidene, 2,4-Dimethoxybenzylidene, 3,4-Dimethoxybenzylidene, 2-Nitrobenzylidene); Cydic Ortho Esters (Methoxymethylene, Ethoxymethylene, Dimethoxymethylene, 1-Methoxyethylidene, 1-Ethoxyethylidine, 1,2-Dimethoxyethylidene, α-Methoxybenzylidene, 1-(N,N-Dimethylamino)ethylidene Derivative, α-(N,N-Dimethylamino)benzylidene Derivative, 2-Oxacyclopentylidene); Silyl Derivatives (Di-t-butylsilylene Group, 1,3-(1,1,3,3-Tetraisopropyldisiloxanylidene), and Tetra-t-butoxydisiloxane-1,3-diylidene), Cyclic Carbonates, Cyclic Boronates, Ethyl Boronate and Phenyl Boronate.

More typically, 1,2-diol protecting groups include those shown in Table A, still more typically, epoxides, acetonides, cyclic ketals and aryl acetals.

TABLE A

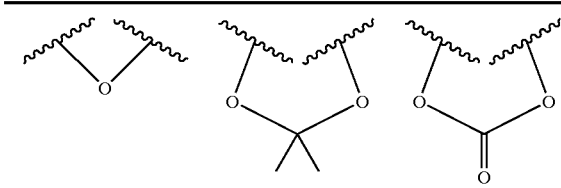

TABLE A-continued

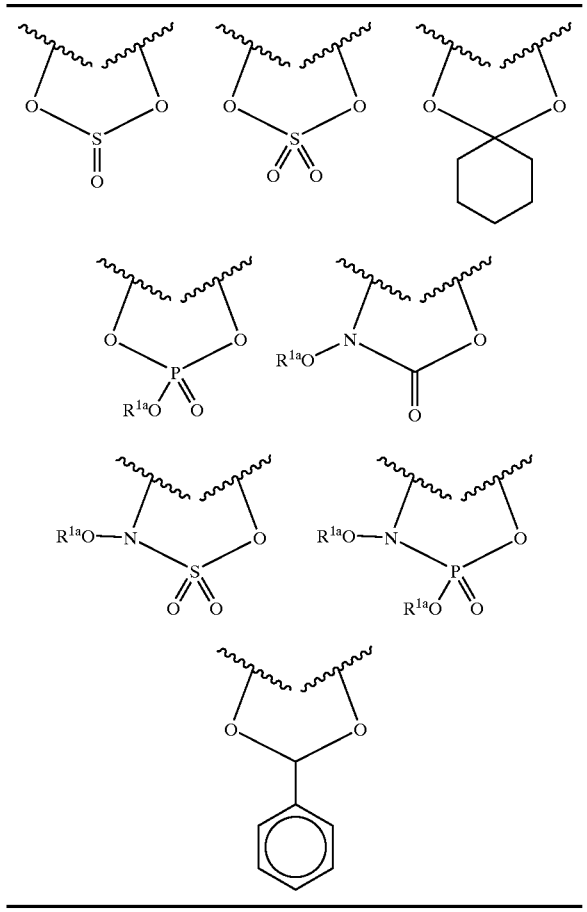

wherein $R^{1a}$ is $C_1$–$C_6$ alkyl.

"Alkyl" as used herein, unless stated to the contrary, is $C_1$–$C_6$ hydrocarbon containing normal, secondary, tertiary or cyclic carbon atoms. Examples are methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, $CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2H(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$) 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$). Typical alkyls are methyl, ethyl, 1-propyl, and 2-propyl.

$R^2$ is H, F, —$OR^1$, or —$OR^6$. Typically $R^2$ is H, or —$OR^1$, more typically, H or —OH, still more typically, —OH.

$R^6$ is

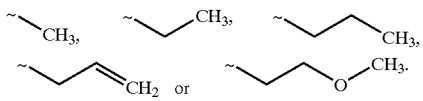

$R^3$ is H or —$CH_3$. Typically $R^3$ is —$CH_3$.

Each $R^4$ of formula I and II is independently H or an amine protecting group, or both $R^4$ groups of formula I are taken together to form a cyclic amine protecting group. Typically, each $R^4$ is H.

$R^4$ amino protecting groups are described by Greene at pages 315–385. They include Carbamates (methyl and ethyl, 9-fluorenylmethyl, 9(2-sulfo)fluoroenylmethyl, 9-(2,7-dibromo)fluorenylmethyl, 2,7-di-t-buthyl-[9-(10,10-dioxo-10,10,10,10-tetrahydrothioxanthyl)]methyl, 4-methoxyphenacyl); Substituted Ethyl (2,2,2-trichoroethyl, 2-trimethylsilylethyl, 2-phenylethyl, 1-(1-adamantyl)-1-methylethyl, 1,1-dimethyl-2-haloethyl, 1,1-dimethyl-2,2-dibromoethyl, 1,1-dimethyl-2,2,2-trichloroethyl, 1-methyl-1-(4-biphenylyl)ethyl, 1-(3,5-dit-butylphenyl)-1-methylethyl, 2-(2'- and 4'-pyridyl)ethyl, 2-(N,N-dicyclohexylcarboxamido)ethyl, t-butyl, 1-adamantyl, vinyl, allyl, 1-isopropylallyl, cinnamyl, 4-nitrocinnamyl, 8-quinolyl, N-hydroxypiperidinyl, alkyldithio, benzyl, p-methoxybenzyl, p-nitrobenzyl, p-bromobenzyl, p-chorobenzyl, 2,4-dichlorobenzyl, 4-methylsulfinylbenzyl, 9-anthrylmethyl, diphenylmethyl); Groups With Assisted Cleavage (2-methylthioethyl, 2-methylsulfonylethyl, 2-(p-toluenesulfonyl)ethyl, [2-(1,3-dithianyl)]methyl, 4-methylthiophenyl, 2,4-dimethylthiophenyl, 2-phosphonioethyl, 2-triphenylphosphonioisopropyl, 1,1-dimethyl-2-cyanoethyl, m-choro-p-acyloxybenzyl, p-(dihydroxyboryl)benzyl, 5-benzisoxazolylmethyl, 2-(trifluoromethyl)-6-chromonylmethyl); Groups Capable of Photolytic Cleavage (m-nitrophenyl, 3,5-dimethoxybenzyl, nitrobenzyl, 3,4-dimethoxy-6-nitrobenzyl, phenyl(o-nitrophenyl)methyl); Urea-Type Derivatives (phenothiazinyl-(10)-carbonyl, N'-p-toluenesulfonylaminocarbonyl, N'-phenylaminothiocarbonyl); Miscellaneous Carbamates (t-amyl, S-benzyl thiocarbamate, p-cyanobenzyl, cyclobutyl, cyclohexyl, cyclopentyl, cyclopropylmethyl, p-decyloxybenzyl, diisopropylmethyl, 2,2-dimethoxycarbonylvinyl, o-(N,N-dimethylcarboxamido) benzyl, 1,1-dimethyl-3-(N,N-dimethylcarboxamido)propyl, 1,1-dimethylpropynyl, di(2-pyridyl)methyl, 2-furanylmethyl, 2-lodoethyl, Isobornyl, Isobutyl, Isonicotinyl, p-(p'-Methoxyphenylazo)benzyl, 1-methylcyclobutyl, 1-methylcydohexyl, 1-methyl-1-cyclopropylmethyl, 1-methyl-1-(3,5-dimethoxyphenyl) ethyl, 1-methyl-1-(p-phenylazophenyl)ethyl, 1-methyl-1-phenylethyl, 1-methyl-1-(4-pyridyl)ethyl, phenyl, p-(phenylazo)benzyl, 2,4,6-tri-t-butylphenyl, 4-(trimethylammonium)benzyl, 2,4,6-trimethylbenzyl); Amides (N-formyl, N-acetyl, N-choroacetyl, N-trichoroacetyl, N-trifluoroacetyl, N-phenylacetyl, N-3-phenylpropionyl, N-picolinoyl, N-3-pyridylcarboxamide, N-benzoylphenylalanyl, N-benzoyl, N-p-phenylbenzoyl); Amides With Assisted Cleavage (N-o-nitrophenylacetyl, N-o-nitrophenoxyacetyl, N-acetoacetyl, (N'-dithiobenzyloxycarbonylamino)acetyl, N-3-(p-hydroxyphenyl)propionyl, N-3-(o-nitrophenyl)propionyl, N-2-methyl-2-(o-nitrophenoxy)propionyl, N-2-methyl-2-(o-phenylazophenoxy)propionyl, N-4-chlorobutyryl, N-3-methyl-3-nitrobutyryl, N-o-nitrocinnamoyl, N-acetylmethionine, N-o-nitrobenzoyl, N-o-(benzoyloxymethyl)benzoyl, 4,5-diphenyl-3-oxazolin-2-one); Cyclic Imide Derivatives (N-phthalimide, N-dithiasuccinoyl, N-2,3-diphenylmaleoyl, N-2,5-dimethylpyrrolyl, N-1,1,4,4-tetramethyldisilylazacyclopentane adduct, 5-substituted 1,3-dimethyl-1,3,5-triazacyclohexan-2-one, 5-substituted 1,3-dibenzyl-1,3-5-triazacyclohexan-2-one, 1-substituted 3,5-dinitro-4-pyridonyl); N-Alkyl and N-Aryl Amines (N-methyl, N-allyl, N-[(2-(trimethylsilyl)ethoxy]methyl, N-3-acetoxypropyl, N-(1-isopropyl-4-nitro-2-oxo-3-pyrrolin-3-yl), Quaternary Ammonium Salts, N-benzyl, N-di(4-methoxyphenyl)methyl, N-5-dibenzosuberyl, N-triphenylmethyl, N-(4-methoxyphenyl)diphenylmethyl, N-9-phenylfluorenyl, N-2,7-dichloro-9-fluorenylmethylene, N-ferrocenylmethyl, N-2-picolylamine N'-oxide), Imine Derivatives (N-1,1-dimethylthiomethylene, N-benzylidene, N-p-methoxybenylidene, N-diphenylmethylene, N-[(2-pyridyl)mesityl]methylene, N,(N',N'-dimethylaminomethylene, N,N'-isopropylidene, N-p-nitrobenzylidene, N-salicylidene, N-5-chlorosalicylidene, N-(5-chloro-2-hydroxyphenyl)phenylmethylene, N-cyclohexylidene); Enamine Derivatives (N-(5,5-dimethyl-3-oxo-1-cyclohexenyl)); N-Metal Derivatives (N-borane derivatives, N-diphenylborinic acid derivatives, N-[phenyl(pentacarbonylchromium- or -tungsten)]carbenyl, N-copper or N-zinc chelate); N-N Derivatives (N-nitro, N-nitroso, N-oxide); N-P Derivatives (N-diphenylphosphinyl, N-dimethylthiophosphinyl, N-diphenylthiophosphinyl, N-dialkyl phosphoryl, N-dibenzyl phosphoryl, N-diphenyl phosphoryl); N-Si Derivatives; N-S Derivatives; N-Sulfenyl Derivatives (N-benzenesulfenyl, N-o-nitrobenzenesulfenyl, N-2,4-dinitrobenzenesulfenyl, N-pentachlorobenzenesulfenyl, N-2-nitro-4-methoxybenzenesulfenyl, N-triphenylmethylsulfenyl, N-3-nitropyridinesulfenyl); and N-sulfonyl Derivatives (N-p-toluenesulfonyl, N-benzenesulfonyl, N-2,3,6-trimethyl-4-methoxybenzenesulfonyl, N-2,4,6-trimethoxybenzenesulfonyl, N-2,6-dimethyl-4-methoxybenzenesulfonyl, N-pentamethylbenzenesulfonyl, N-2,3,5,6,-tetramethyl4-methoxybenzenesulfonyl, N-4-methoxybenzenesulfonyl, N-2,4,6-trimethylbenzenesulfonyl, N-2,6-dimethoxy-4-methylbenzenesulfonyl, N-2,2,5,7,8-pentamethylchroman-6-sulfonyl, N-methanesulfonyl, N-β-trimethylsilyethanesulfonyl, N-9-anthracenesulfonyl, N-4-(4',8'-dimethoxynaphthylmethyl)benzenesulfonyl, N-benzylsulfonyl, N-trifluoromethylsulfonyl, N-phenacylsulfonyl).

$R^5$ is H, —$CH_3$ or —C≡C—$CH_3$. Typically $R^5$ is —$CH_3$.

In another embodiment of the invention, when the compound is of: formula I wherein each of $R^1$, $R^2$, $R^3$, $R^4$, and $R^5$ are H; or formula II wherein each of $R^1$, $R^2$, $R^3$, and $R^4$ are H, and $R^5$ is —$CH_3$; then the compound is not of the formula:

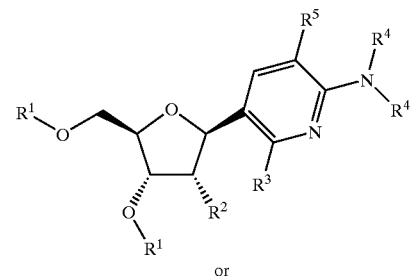

In another embodiment the compound is of formula III or IV.

In another embodiment the compound is of formula III or IV, with the proviso that the compound is not of formula I wherein each of $R^1$, $R^2$, $R^3$, $R^4$, and $R^5$ are H; or of formula II wherein each of $R^1$, $R^2$, $R^3$, and $R^4$ are H, and $R^5$ is —$CH_3$.

In another embodiment the compound is of formula I or II wherein $R^3$ is —$CH_3$.

In another embodiment the compound is of formula I.

In another embodiment the compound is of formula III.

In another embodiment the compound is of formula III with the proviso that the compound is not of formula III wherein each of $R^1$, $R^2$, $R^3$, $R^4$, and $R^5$ are H. Typically, $R^3$ is —$CH_3$.

In another embodiment the compound is of the formula:

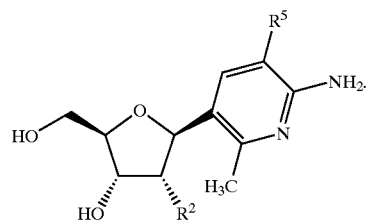

In another embodiment the composition of formula V wherein:

$R^2$ is H and $R^5$ is H;

R2 is H and $R^5$ is —$CH_3$;

$R^2$ is H and $R^5$ is C≡C—$CH_3$;

$R^2$ is —OH and $R^5$ is H;

$R^2$ is —OH and $R^5$ is —$CH_3$; or $R^2$ is —OH and $R^5$ is —C≡CH$_3$. Typically $R^2$ is H and $R^5$ is —$CH_3$.

Stereoisomers

The compounds of the invention are enriched or resolved optical isomers at any or all asymmetric atoms. For example, the chiral centers apparent from the depictions are provided as the chiral isomers or racemic mixtures. Both racemic and diasteromeric mixtures, as well as the individual optical isomers isolated or synthesized, substantially free of their enantiomeric or diastereomeric partners, are all within the scope of the invention. The racemic mixtures are separated into their individual, substantially optically pure isomers through well-known techniques such as, for example, the separation of diastereomeric salts formed with optically active adjuncts, e.g., acids or bases followed by conversion back to the optically active substances. By way of example and not limitation, methods of resolving individual enantiomers are described in "Enantiomers, Racemates, and resolutions", Jean Jacques, Andre Collet, and Samuel H. Wilen (Krieger Publishing Company, Malabar, Fla., 1991, ISBN 0-89464-618-4). In particular, Part 2, Resolution of Enantiomer Mixture, pages 217–435; more particularly, section 4, Resolution by Direct Crystallization, pages 217–251, section 5, Formation and Separation of Diastereomers, pages 251–369, section 6, Crystallization-Induced Asymmetric Transformations, pages 369–378, and section 7, Experimental Aspects and Art of Resolutions, pages 378–435; still more particularly, section 5.1.4, Resolution of Alcohols. Transformation of Alcohols into Salt-Forming Derivatives, pages 263–266, section 5.2.3 Covalent Derivatives of Alcohols, Thiols, and Phenols, pages 332–335, and section 5.2.7, Chromatographic Behavior of Covalent Diastereomers, pages 348–354, are cited as examples of the skill of the art. In most instances, the desired optical isomer is synthesized by means of stereospecific reactions, beginning with the appropriate stereoisomer of the desired starting material.

Exemplary Enumerated Compounds

By way of, example and not limitation, embodiment compounds are named below in tabular format (Table 5). Generally, each compound is depicted as a substituted nucleus in which the nucleus is designated by capital letter and each substituent is designated in order by number or capital letter. Table 1 is a schedule of nuclei. Each nucleus is given an alphabetical designation from Table 1, and this designation appears first in each compound name. Similarly, Tables 2, 3, and -4 list the selected $R^2$, $R^3$ and $R^5$ substituents, again by number or capital letter designation. Accordingly, each named compound will be depicted by a capital letter designating the nucleus from Table 1, followed by a number designating the $R^2$ substituent, a capital letter designating the $R^3$ substituent, and a number designating the $R^5$ substituent. Thus, the compound of claim 12 is represented by A.1.B.2.

TABLE 1

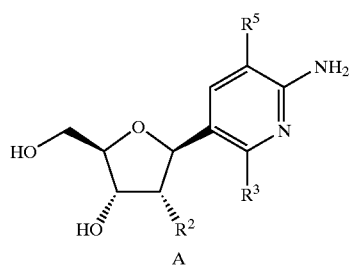

A

TABLE 1-continued

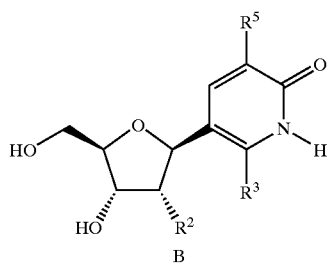

B

TABLE 2

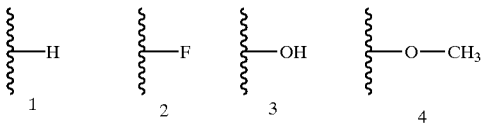

TABLE 3

TABLE 4

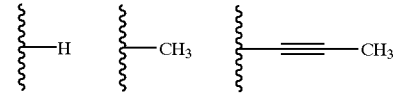

TABLE 5

| | | | | | | | | |
|---|---|---|---|---|---|---|---|---|
| A.1.A.1; | A.1.A.2; | A.1.A.3; | A.1.B.1; | A.1.B.2; | A.1.B.3; | A.2.A.1; | A.2.A.2; | |
| A.2.A.3; | A.2.B.1; | A.2.B.2; | A.2.B.3; | A.3.A.1; | A.3.A.2; | A.3.A.3; | A.3.B.1; | |
| A.3.B.2; | A.3.B.3; | A.4.A.1; | A.4.A.2; | A.4.A.3; | A.4.B.1; | A.4.B.2; | A.4.B.3; | |
| A.5.A.1; | A.5.A.2; | A.5.A.3; | A.5.B.1; | A.5.B.2; | A.5.B.3; | A.6.A.1; | A.6.A.2; | |
| A.6.A.3; | A.6.B.1; | A.6.B.2; | A.6.B.3; | A.7.A.1; | A.7.A.2; | A.7.A.3; | A.7.B.1; | |
| A.7.B.2; | A.7.B.3; | A.8.A.1; | A.8.A.2; | A.8.A.3; | A.8.B.1; | A.8.B.2; | A.8.B.3; | B.1.A.1; |
| B.1.A.2; | B.1.A.3; | B.1.B.1; | B.1.B.2; | B.1.B.3; | B.2.A.1; | B.2.A.2; | B.2.B.1; | |
| B.2.B.2; | B.2.B.3; | B.3.A.1; | B.3.A.2; | B.3.A.3; | B.3.B.1; | B.3.B.2; | B.3.B.3; | B.4.A.1; |
| B.4.A.2; | B.4.A.3; | B.4.B.1; | B.4.B.2; | B.4.B.3; | B.5.A.1; | B.5.A.2; | B.5.A.3; | B.5.B.1; |
| B.5.B.2; | B.5.B.3; | B.6.A.1; | B.6.A.2; | B.6.A.3; | B.6.B.1; | B.6.B.2; | B.6.B.3; | B.7.A.1; |
| B.7.A.2; | B.7.A.3; | B.7.B.1; | B.7.B.2; | B.7.B.3; | B.8.A.1; | B.8.A.2; | B.8.A.3; | B.8.B.1; |
| B.8.B.2; | B.8.B.3 | | | | | | | |

Salts and Hydrates

The compositions of this invention optionally comprise salts of the compounds herein, for example, $Na^+$, $Li^+$, $K^+$, $Ca^{++}$ and $Mg^{++}$. Such salts may include those derived by combination of appropriate cations such as alkali and alkaline earth metal ions or ammonium and quaternary amino ions with an acid anion moiety. Monovalent salts are preferred if a water soluble salt is desired.

Metal salts typically are prepared by reacting the metal hydroxide with a compound of this invention. Examples of metal salts which are prepared in this way are salts containing $Li^+$, $Na^+$, and $K^+$. A less soluble metal salt can be precipitated from the solution of a more soluble salt by addition of the suitable metal compound.

In addition, salts may be formed from acid addition of certain organic and inorganic acids, e.g., HCl, HBr, $H_2SO_4$, or organic sulfonic acids, to basic centers, typically amines. Finally, it is to be understood that the compositions herein comprise compounds of the invention in their un-ionized, as well as zwitterionic form, and combinations with stoiochimetric amounts of water as in hydrates.

Also included within the scope of this invention are the salts of the parental compounds with one or more amino acids. Any of the amino acids described above are suitable, especially the naturally-occurring amino acids found as protein components, although the amino acid typically is one bearing a side chain with a basic or acidic group, e.g., lysine, arginine or glutamic acid, or a neutral group such as glycine, serine, threonine, alanine, isoleucine, or leucine.

Oligonucleotides

Another embodiment of the present invention is directed to oligomers capable of triple helix formation comprising a multiplicity of nucleosides linked by internucleoside linkages wherein at least one nucleoside is a 2-aminopyridine and 2-pyridone C-nucleosides.

The principals of triplex binding and assays utilizing triplex binding have been described in detail elsewhere and will not be repeated here. By way of example and not limitation, see Froehier, B. and Jones, R. J., U.S. Pat. No. 5,484,908, Jan. 16, 1996, in particular column 1, line 1, to column 3, line 55, and Cantor, C. R and Smith, C. L., U.S. Pat. No. 5,482,836, Jan. 9, 1996, in particular column 1, line 30, to column 2, line 58.

An oligonucleotide capable of binding specifically to a duplex oligonucleotide is an oligonucleotide that binds in a triplex mode to a given target duplex. Specificity is determined by the particular application. Generally, selectivity is expressed as the ratio of oligonucleotide bound to the target section of duplex vs. oligonucleotide bound to another section of duplex. Typically >1:1 binding is selective binding, more typically >10:1, still more typically >100:1. In some applications binding ratios higher than 1000:1 or 10000:1 are obtained.

As used herein, oligonucleotide means single stranded or double stranded DNA or RNA, and analogs of DNA or RNA and plasmids comprising oligonucleotides. In general, relatively large nucleic acids such as plasmids or mRNAs will carry one or more genes that are to be expressed in a transfected cell, while comparatively small nucleic acids, i.e., typical oligonucleotides, will comprise (1) a base sequence that is complementary (via Watson Crick or Hoogsteen binding) to a DNA or RNA sequence present in the cell or (2) a base sequence that permits oligonucleotide binding to a molecule inside a cell such as a peptide, protein or glycoprotein. Exemplary RNAs include ribozymes and antisense RNA sequences that are complementary to a target RNA sequence in a cell.

Oligonucleotides include single stranded unmodified DNA or RNA comprising (a) the purine or pyrimidine bases guanine, adenine, cytosine, thymine and/or uracil; (b) ribose or deoxyribose; and (c) a phosphodiester group that linkage adjacent nucleoside moieties. Oligonucleotides typically comprise 2 to about 100 or 3 to about 100 linked nucleosides. Typical oligonucleotides comprise size ranges such as 2-10, 2-15, 2-20, 2-25, 2-30, 7-15, 7-20, 7-30 or 7-50 linked nucleotides. Oligonucleotides can be linear, circular, branched or double-stranded. Oligonucleotides are usually linear with uniform polarity but, when regions of inverted polarity are present, such regions comprise no more than one polarity inversion per 10 nucleotides. One inversion per 20 nucleotides is typical. Antisense oligonucleotides generally will comprise a sequence of about 7–50 bases, usually about 8–30 bases. The oligonucleotide base sequence is usually complementary or substantially complementary to a cognate DNA or RNA base sequence present in the cell. The size of nucleic acid of the invention is limited only by the size of molecules that reasonably can be prepared by conventional means.

Oligonucleotides also include DNA or RNA comprising one or more covalent modifications. Covalent modifications include (a) replacement of the phosphodiester group with a nonphosphorus moiety such as —O—$CH_2$—O—, —S—$CH_2$—O— or —O—$CH_2$—S—, and (c) replacement of the phosphodiester group with a phosphate analog such as —O—P(S)(O)—O—(phosphorothioate linkage), —O—P(S)(S)—O—, —O—P($CH_3$)(O)—O— or —O—P(NHR13)(O)—O— where $R^{13}$ is alkyl ($C_{1-6}$), or an alkyl ether ($C_{1-6}$). Oligonucleotides include modified oligonucleotides having a substitution at about 20–100%, more often about 40–100% and usually about 80%–100% of the phosphodiester groups in unmodified DNA or RNA. Such modified oligonucleotides optionally also have 20–100%, more often about 40–100% or about 80%–100% of the pyrimidine bases substituted with (1-propynyl)uracil or 5-(1-propynyl) cytosine. Oligonucleotides include covalent modification or isomers of ribose or deoxyribose such as morpholino, arabinose, 2'-fluororibose, 2'-fluoroarabinose, 2'-methylribose or 2'-allylribose. Oligonucleotides and methods to synthesize them have been described (for example see: PCT/US90/03138, PCT/US90/06128, PCT/US90/06090, PCT/US90/06110, PCT/US92/03385, PCT/US91/08811, PCT/US91/03680, PCT/US91/06855, PCT/US91/01141, PCT/US92/10115, PCT/US92/10793, PCT/US93/05110, PCT/US93/05202, PCT/US92/04294, US94/04013, WO86/05518, WO89/12060, WO91/08213, WO90/15065, WO91/15500, WO92/02258, WO92/20702, WO92/20822, WO92/20823, U.S. Pat. No. 5,214,136 and Uhlmann et al. *Chem. Rev.* (1990) 90:543.

Linkage means a moiety suitable for coupling adjacent nucleomonomers and includes both phosphorus-containing moieties and non phosphorus-containing moieties such as formacetal, thioformacetal, riboacetal and the like. A linkage usually comprises 2 or 3 atoms between the 5' position of a nucleotide and the 2' or 3' position of an adjacent nucleotide. Linkages between the 5' and 2' positions will usually not contain phosphorus.

A purine or pyrimidine base means a heterocyclic moiety suitable for incorporation into an oligonucleotide. It can be in the α or β anomer configuration. Purine or pyrimidine bases are moieties that bind to complementary nucleic acid sequences by Watson-Crick or Hoogsteen base pair rules. Bases need not always increase the binding affinity of an oligonucleotide for binding to its complementary sequence at least as compared to bases found in native DNA or RNA. However, such modified bases preferably are not incorporated into an oligomer to such an extent that the oligonucleotide is unable to bind to complementary sequences to produce a detectably stable duplex or triplex. Purine or pyrimidine bases usually pair with a complementary purine or pyrimidine base via 1, 2 or 3 hydrogen bonds. Such purine or pyrimidine bases are generally the purine, pyrimidine or related heterocycles shown in formulas G-I.

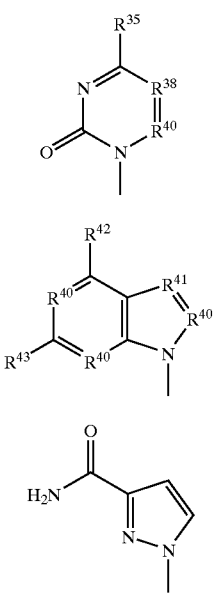

-continued

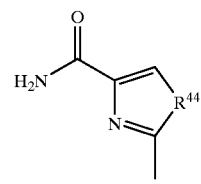

wherein $R^{35}$ is H, —OH, F, Cl, Br, I, —OR$^{36}$, —SH, —SR$^{36}$, —NH$_2$, or —NHR$^{37}$;

$R^{36}$ is $C_1$–$C_6$ alkyl (including —CH$_3$, —CH$_2$CH$_3$ and —C$_3$H$_7$), —CH$_2$CCH (2-propynyl) and —CH$_2$CHCH$_2$;

$R^{37}$ is $C_1$–$C_6$ alkyl including —CH$_3$, —CH$_2$CH$_3$, —CH$_2$CCH, —CH$_2$CHCH$_2$ –C$_3$H$_7$;

$R^{38}$ is N, CF, CCl, CBr, CI, CR$^{39}$ or CSR$^{39}$, COR$^{39}$;

$R^{39}$ is H, $C_1$–$C_9$ alkyl, $C_2$–$C_9$ alkenyl, $C_2$–$C_9$ alkynyl or $C_7$–$C_9$ aryl-alkyl unsubstituted or substituted by OH, O, N, F, Cl, Br or I including —CH$_3$, —CH$_2$CH$_3$, —CHCH$_2$, —CHCHBr, —CH$_2$CH$_2$Cl, —CH$_2$CH$_2$F, —CH$_2$CCH, —CH$_2$CHCH$_2$, —C$_3$H$_7$, —CH$_2$OH, —CH$_2$OCH$_3$, C—H$_2$OC$_2$H$_5$, —CH$_2$OCCH, —CH$_2$CH$_2$CHCH$_2$, —CH$_2$C$_3$H$_7$, —CH$_2$CH$_2$OH, —CH$_2$CH$_2$OCH$_3$, —CH$_2$CH$_2$OC$_2$H$_5$, —CH$_2$CH$_2$OCCH, —CH$_2$CH$_2$OCH$_2$CHCH$_2$, —CHCH$_2$OC$_3$H$_7$;

$R^{40}$ is N, CBr, CI, CCl, CH, C(CH$_3$), C(CH$_2$CH$_3$) or C(CH$_2$CH$_2$CH$_3$);

$R^{41}$ is N, CH, CBr, CCH$_3$, CCN, CCF$_3$, CC≡CH or CC(O)NH$_2$;

$R^{42}$ is H, OH, NH$_2$, SH, SCH$_3$, SCH$_2$CH$_3$, SCH$_2$CCH, SCH$_2$CHCH$_2$, SC$_3$H$_7$, NH(CH$_3$), N(CH$_3$)$_2$, NH(CH$_2$CH$_3$), N(CH$_2$CH$_3$)$_2$, NH(CH$_2$CCH), NH(CH$_2$CHCH$_2$), NH(C$_3$H$_7$) or F, Cl, Br or I;

$R^{43}$ is H, OH, F, Cl, Br, I, SCH$_3$, SCH$_2$CH$_3$, SCH$_2$CCH, SCH$_2$CHCH$_2$, SC$_3$H$_7$, OR$^{16}$, NH$_2$, or NHR$^{37}$; and $R^{44}$ is O, S or Se.

Exemplary bases include adenine, cytosine, guanine, hypoxanthine, inosine, thymine, uracil, xanthine, 2-aminopurine, 2,6-diaminopurine, 5-(4-methylthiazol-2-yl) uracil, 5-(5-methylthiazol-2-yl)uracil, 5-(4-methylthiazol-2-yl)cytosine, 5-(5-methylthiazol-2-yl)cytosine and the like.

Also included are alkylated or alkynylated bases having substitutions at, for example, the 5 position of pyrimidines that results in a pyrimidine base other than uracil, thymine or cytosine, i.e., 5-methylcytosine, 5-(1-propynyl)cytosine, 5-(1-butynyl)cytosine, 5-(1-butynyl)uracil, 5-(1-propynyl) uracil and 7-(1-propynyl)-7-deazaguanine. Base analogs and their use in oligomers have been described (see for example, U.S. Application Ser. No. 08/123,505; WO 92/10115; WO 91/08811; WO 92/09195; WO 93/10820; WO 92/09705; WO 92/02258; Nikiforov, T. T., et al, *Tet Lett* (1992) 33:2379–2382; Clivio, P., et al, *Tet Lett* (1992) 33:65–68; Nikiforov, T. T., et al, *Tet Lett* (1991) 32:2505–2508; Xu, Y.-Z, et al, *Tet Lett* (1991) 32:2817–2820; Clivio, P., et al, *Tet Lett* (1992) 33:69–72; Connolly, B. A., et al, *Nucl Acids Res* (1989) 17:4957–4974). Oligonucleotides having varying amounts of bases analogs such as 5-methylcytosine, 5-(1-propynyl)cytosine, 5-(1-butynyl)cytosine or 5-(1-butynyl) uracil, 5-(1-propynyl)uracil or 7-(1-propynyl)-7-deazaguanine, e.g., about 20–80%, usually about 80–100% of the natural bases are substituted with the corresponding analogs.

Triplex-Affinity Capture

Another aspect of the invention is directed to a method for purifying intact DNA using intermolecular triple-helix formation and solid phase separation. The details of the method have been described elsewhere and will not be repeated here. By way of example and not limitation, see Cantor, C. R and Smith, C. L., U.S. Pat. No. 5,482,836, Jan. 9, 1996. In this triplex-affinity capture (TAC) method, the DNA being detected in the assay is intact double stranded DNA and the method can be used to capture sequence specific plasmid DNAs. Essentially, the target DNA sequence is a double stranded homopurine-homopyrimidine helix. Nevertheless, the method may be extended by the use of some permissiveness mismatches in triple-helix formation (Griffin, L. C., et al. *Science* (1989) 245:967–971 and Belotserkovskii, B. D., et al. *Nucleic Acids Res.* (1990) 18:6621–6624), alternate strand triple-helix formation (Horne, D. A., et al. *J. M. Chem. Soc.* (1990) 112:2435–2438), other types of triple-helices (Cooney, M., et al. *Science* (1988) 241:456–459; Kohwi, Y., et al. *Proc. Natl. Acad. Sci. USA* (1988) 85:3781–3785; Letai, A. G., et al. *Biochemistry* (1988) 27:9108–9112; Bernues, J., et al. *EMBO J.* (1989) 8:2087–2094; Beal, P. A., et al. *Science* (1991) 251:1360–1363; Pilch, D. S., et al. *Biochemistry* (1991) 30:6081–6087; Orson, F. M., et al. *Nucleic Acids Res.* (1991) 19:3435–3441), including ones formed by recombinase proteins (Hsieh, P., et al. *Genes Dev.* (1990) 4:1951–1963; Rao, B. J., et al. *Proc. Natl. Acad. Sci. USA* (1991) 88:2984–2988) and artificial base analogs.

The TAC procedure of the invention is especially appropriate for isolating (dT-dC)n·(dG-dA)n dinucleotide repeats from human genome. This sequence is a member of so-called "microsatellite" DNAs distributed throughout mammalian genomes (Manor, H., et al. *J. Mol. Evol.* (1988) 27:96–101; Wong, A. K. C., et al. *Chromosoma* (1990) 99:344–351). It is often hyper-variable in the number of repeat units (n) from individual-to-individual and thus provides highly informative DNA markers for genetic linkage mapping (Tautz, D., *Nucleic Acids Res.* (1989) 17:6463–6471; Love, J. M., et al. *Nucleic Acids Res.* (1990) 18:4123–4130; Moore, S. S., et al. *Genomics* (1991) 10:654–660; Weber, J. L. (1990) in Genome Analysis, eds. Davies, K. E. et al. (Cold Spring Harbor Lab., Cold Spring Harbor, N.Y.). Vol. 1, pp. 159–181). The TAC method may also be used for the effective enrichment of triplex forming single copy sequences from yeast and more complex genomes using the appropriate probes. The use of G and a novel artificial base analog (Kiessling, L. L., et al. *Biochemistry* (1992) 31:2829–2834) in the third strand has broadened the triplex recognition capability to allow one to find a target for TAC in natural non-tagged sequences with much ease.

The TAC method for purifying a particular double strand of DNA comprises contacting the sample with an oligonucleotide of the invention coupled either directly or indirectly to a first recognition molecule of a specific molecular recognition system. The oligonucleotide is designed to specifically form a triple helix with the target DNA. Methods for designing such oligonucleotides depend on the target DNA. Acceptable methods are set forth in Kiessling, L. L., et al. *Biochemistry* (1992) 31:2829–2834; Durland, R. H., et al. *Biochemistry* (1991) 30:9246–9255; Beal, P. A., et al. *Nucleic Acids Res.* (1992) 20:2773–2776; Giovannangeli, C., et al. *Proc. Natl. Acad. Sci.* (1992) 89:8631–8635; Beal, P. A., et al., *J. Am. Chem. Soc.* (1992) 114:4976–4982. Oligonucleotides which contain deoxyuracil for thymine at least along part of the chain are acceptable oligonucleotides. Oligonucleotide backbone analogs such as polyamide nucleic acids and phosphotriesters will form a triplex with double stranded DNA and can also be used in the TAC method of the invention.

The triplexes formed between the specific oligonucleotides of the invention and the target DNA molecules containing the corresponding homopurine-homopyrimidine sequences are subsequently contacted with a solid carrier to which is either directly or indirectly fixed a second recognition molecule belonging to the same molecular recognition system as the first recognition molecule coupled to the oligonucleotide. The second recognition molecule is a molecule which will specifically bind to the first recognition molecule. The solid phase is subsequently separated from the reaction medium where the binding occurred and therefore is also separated from any remaining non-triplexed nucleic adds. Finally, the target DNAs are recovered in intact double stranded form by treating the separated solid phase bearing the triple-helix with a reagent that breaks the bonds between the oligonucleotide and the particular DNA but not between the double helix DNA. The particular DNA is then recovered.

Using several methods well-known in the art including electrophoresis and fluorometry, the TAC method can also be used to determine the presence or absence of a particular double stranded DNA in a sample by testing for the presence of the particular DNA in the eluate after the triple helix separation step.

Another aspect of the invention is directed to improvements in a triplex-affinity capture purification wherein the improvement comprises employing as -the coupled oligonucleotide an oligonucleotide containing one or more of the modified oligonucleosides ( i.e. a 2-aminopyridine and 2-aminopyridone C-nucleoside) of the present invention. One example of the triplex-affinity capture purification of this embodiment is described in Cantor, C. R. and Smith, C. L., U.S. Pat. No. 5,482,836, Jan. 9, 1996, in particular one or more of the methods described at column 21, line 22, to column 26, line 39.

Assays

Another embodiment of the present invention is directed to methods of detecting the presence, absence or amount of a particular DNA duplex in a sample suspected of containing DNA comprising contacting the sample with an oligomer of the invention under conditions wherein a triple helix is formed between the oligomer and the particular DNA duplex.

The conventional aspects of oligonucleotide hybridization assays, in particular, the principals of triplex binding and assays utilizing triplex binding, have been described in detail elsewhere and will not be repeated here. By way of example and not limitation, see Froehler, B. and Jones, R. J., U.S. Pat. No. 5,484,908, Jan. 16, 1996, in particular column 1, line 1, to column 3, line 55, and column 20, line 38, to column 21, line 18.

Generally, the oligomers of the invention may be used as diagnostic reagents to detect the presence or absence of the target gene sequences to which they specifically bind. Such diagnostic tests are conducted by hybridization through either double or triple helix formation which is then detected by conventional means. For example, the oligomers may be labeled using radioactive, fluorescent, or chromogenic labels and the presence of label bound to solid support detected. Alternatively, the presence of a double or triple helix may be detected by antibodies which specifically recognize these forms. Means for conducting assays using such oligomers as probes are generally known.

The use of oligomers containing the modified bases as diagnostic agents by triple helix formation is advantageous since triple helices form under mild conditions and the assays may thus be carried out without subjecting test specimens to harsh conditions. Diagnostic assays based on detection of RNA for identification of bacteria, fungi or protozoa sequences often require isolation of RNA from samples or organisms grown in the laboratory, which is laborious and time consuming; as RNA is extremely sensitive to ubiquitous nucleases.

The oligomer probes may also incorporate additional modifications such as altered internucleotide linkages that render the oligomer especially nuclease stable, and would thus be useful for assays conducted in the presence of cell or tissue extracts which normally contain nuclease activity. Oligonucleotides containing terminal modifications often retain their capacity to bind to complementary sequences without loss of specificity (Uhlmann et al., *Chemical Reviews* (1990) 90:543–584). As set forth above, the invention probes may also contain linkers that permit specific binding to alternate DNA strands by incorporating a linker that permits such binding (Home et al., *J. Am Chem Soc* (1990) 112:2435–2437).

Incorporation of base analogs of the present invention into probes that also contain covalent crosslinking agents has the potential to increase sensitivity and reduce background in diagnostic or detection assays. In addition, the use of crosslinking agents will permit novel assay modifications such as (1) the use of the crosslink to increase probe discrimination, (2) incorporation of a denaturing wash step to reduce background and (3) carrying out hybridization and crosslinking at or near the melting temperature of the hybrid to reduce secondary structure in the target and to increase probe specificity. Modifications of hybridization conditions have been previously described (Gamper et al., *Nucleic Acids Res* (1986) 14:9943).

The conventional aspects of oligonucleotide hybridization assays are well known and will not be repeated here.

Additional Uses for the Compounds of This Invention

The compounds of the invention are polyfunctional. As such they represent a unique dass of monomers for the synthesis of polymers. By way of example and not limitation, the polymers prepared from the compounds of this invention include polyamides, polyesters and mixed polyester-polyamides.

The present compounds are used as monomers to provide access to polymers having unique pendent functionalities. The compounds of this invention are useful as comonomers with monomers which do not fall within the scope of the invention. Polymers of the compounds of this invention will have utility as cation exchange agents (polyesters or polyamides) in the preparation of molecular sieves (polyamides), textiles, fibers, films, formed articles and the like. Polymers are prepared by any conventional method, for example, by cross-linking an —OH or —$NH_2$ group of the compounds of the invention with a diacid comonomer. The preparation of these polymers from the compounds of the invention is conventional per se.

The compounds of the invention are also useful as a unique class of polyfunctional surfactants. Particularly when $R^1$ or $R^2$ do not contain hydrophilic substituents and are, for example, alkyl or alkoxy, the compounds have the properties of bi-functional surfactants. As such they have useful surfactant, surface coating, emulsion modifying, rheology modifying and surface wetting properties.

As polyfunctional compounds with defined geometry and carrying simultaneously polar and non-polar moieties, the compounds of the invention are useful as a unique class of phase transfer agents. By way of example and not limitation, the compounds of the invention are useful in phase transfer catalysis and liquid/liquid ion extraction (LIX).

The compounds of the invention optionally contain asymmetric carbon atoms. As such, they are a unique class of chiral auxiliaries for use in the synthesis or resolution of other optically active materials. For example, a racemic mixture of carboxylic acids can be resolved into its component enantiomers by: 1) forming a mixture of diastereomeric esters or amides with a compound of the invention containing an —OH or —$NH_2$ group; 2) separating the diastereomers; and 3) hydrolyzing the ester structure. Further, such a method can be used to resolve the compounds of the invention themselves if optically active acids are used instead of racemic starting materials.

The compounds of this invention are useful as linkers or spacers in preparing affinity absorption matrices, immobilized enzymes for process control, or immunoassay reagents. The compounds herein contain a multiplicity of functional groups that are suitable as sites for cross-linking desired substances. For example, it is conventional to link affinity reagents such as hormones, peptides, antibodies, drugs, and the like to insoluble substrates. These insolublized reagents are employed in known fashion to absorb binding partners for the affinity reagents from manufactured preparations, diagnostic samples and other impure mixtures. Similarly, immobilized enzymes are used to perform catalytic conversions with facile recovery of enzyme. Bifunctional compounds are commonly used to link analytes to detectable groups in preparing diagnostic reagents.

Many functional groups in the compounds of this invention are suitable for use in cross-linking. For example, —OH and —$NH_2$ groups. Suitable protection of reactive groups will be used where necessary while assembling the cross-linked reagent to prevent polymerization of the bifunctional compound of this invention. In general, the compounds here are used by linking them through hydroxyl or amino groups to carboxylic or phosphonic acid groups of the first linked partner, then covalently bonding to the other binding partner through another —OH or —$NH_2$ group. For example a first binding partner such as a steroid hormone is reacted to form an amide bond with the —$NH_2$ group of a compound of this invention and then this conjugate is cross-linked through a hydroxyl to cyanogen bromide activated Sepaharose, whereby immobilized steroid is obtained. Other chemistries for conjugation are well known. See for example Maggio, *Enzyme Immunoassay* (CRC, 1988, pp 71–135) and references cited therein.

The following examples are put forth so as to provide those of ordinary skill in the art with a complete disclosure and description of how to make the compounds and compositions of the invention and are not intended to limit the scope of what the inventors regard as their invention. Efforts have been made to insure accuracy with respect to numbers used (e.g., amounts, temperatures, etc.), but some experimental errors and deviations should be taken into account. Unless indicated otherwise, parts are parts by weight, temperature is in degrees Centigrade, and pressure is at or near atmospheric.

Synthesis of 2-Aminopyridine and 2-pyridone C-nucleosides

The invention is also directed to methods of making the compositions of the invention. The compositions are prepared by any of the applicable techniques of organic synthesis. Many such techniques are well known in the art However, many of the known techniques are elaborated in "Compendium of Organic Synthetic Methods" John Wiley & Sons, New York), Vol. 1, Ian T. Harrison and Shuyen Harrison, 1971; Vol. 2, Ian T. Harrison and Shuyen Harrison, 1974; Vol. 3, Louis S. Hegedus and Leroy Wade, 1977; Vol. 4, Leroy G. Wade, jr., 1980; Vol. 5, Leroy G. Wade, Jr., 1984; and Vol. 6, Michael B. Smith; as well as March, J., "Advanced Organic Chemistry, Third Edition", John Wiley & Sons, New York, 1985), "Comprehensive Organic Synthesis. Selectivity, Strategy & Efficiency in Modem Organic Chemistry. In 9 Volumes", Barry M. Trost, Editor-in-Chief (Pergamon Press, New York, 1993 printing).

A number of exemplary methods for the preparation of the compositions of the invention are provided below. These methods are intended to illustrate the nature of such preparations are not intended to limit the scope of applicable methods.

Generally, the reaction conditions such as temperature, reaction time, solvents, workup procedures, and the like, will be those common in the art for the particular reaction to be performed. The cited reference material, together with material cited therein, contains detailed descriptions of such conditions. Typically the temperatures will be −100° C. to 200° C., solvents will be aprotic or protic, and reaction times will be 10 seconds to 10 days. Workup typically consists of quenching any unreacted reagents followed by partition between a water/organic layer system (extraction) and separating the layer containing the product.

Oxidation and reduction reactions are typically carried out at temperatures near room temperature (about 20° C.), although for metal hydride reductions frequently the temperature is reduced to 0° C. to −100° C., solvents are typically aprotic for reductions and may be either protic or aprotic for oxidations. Reaction times are adjusted to achieve desired conversions.

Condensation reactions are typically carried out at temperatures near room temperature, although for non-equilibrating, kinetically controlled condensations reduced temperatures (0° C. to −100° C.) are also common. Solvents can be either protic (common in equilibrating reactions) or aprotic (common in kinetically controlled reactions).

Standard synthetic techniques such as azeotropic removal of reaction by-products and use of anhydrous reaction conditions (e.g. inert gas environments) are common in the art and will be applied when applicable.

Scheme 1

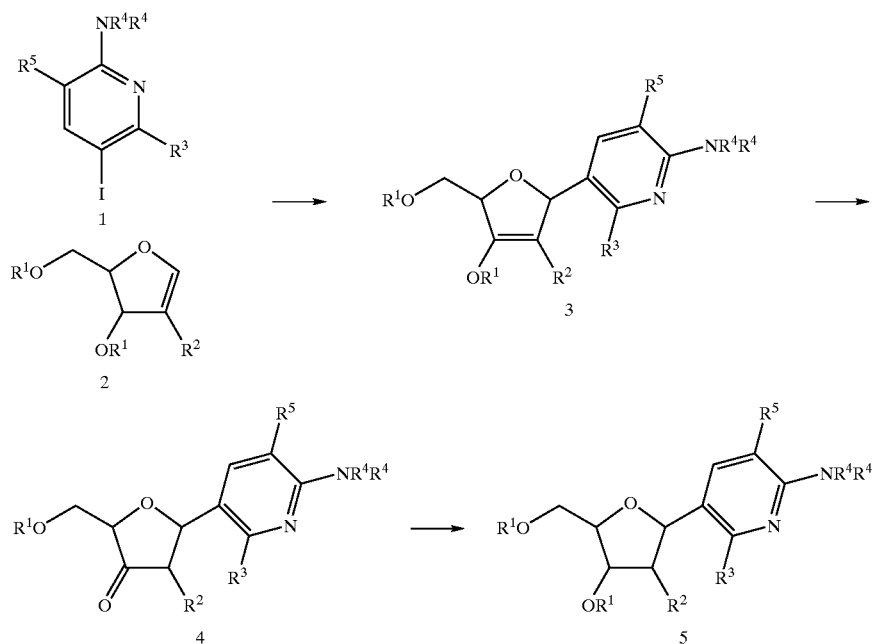

One exemplary method of making the nucleosides of the invention is PATENT depicted in Scheme 1. $R^1$, $R^2$, $R^3$, $R^4$ and $R^5$ are as described above. The $R^1$ group on the 5' O is typically H and the $R^1$ group on the 3' O is usually a hydroxy protecting group stable to the conditions used to prepare compound 3. Typically the protecting group is an acid labile, base stable protecting group. Each $R^4$ is usually H but may be an amine protecting group. $R^2$ is usually H.

Iodopyridine 1 is reacted with olefin 2 to produce compound 3. The reaction is typically accomplished using a metal catalyst, more typically a Palladium catalyst. A suitable solvent is optionally present. Typically an amine solvent ($C_1$-$C_6$ trialkyl amine is usual), optionally in the presence of a cosolvent such as $CH_3CN$. For example the reaction can be performed using $Pd(OAc)_2/Ph_3As$ in $Bu_3N/CH_3CN$.

Compound 3 is reacted to form compound 4. Typically the protecting group is removed. For example if the protecting group is a silyl ether, acid optionally in the presence of a fluoride source is employed. HOAc/TBAF/THF is typical for a TBDPSi group.

The reduction of compound 4 to prepare compound 5 is carried out by any of the usual methods. For example a hydroborating agent such as $NaBH(OAc)_3$ is typical.

Another embodiment of the invention is the method of Scheme 1 wherein the 2-aminopyridine compound 1 is replaced with the corresponding 2-pyridone to produce the 2-pyridone version of compound 5.

Modifications of each of the above schemes leads to various analogs of the specific exemplary materials produced above. The above cited citations describing suitable methods of organic synthesis are applicable to such modifications.

In each of the above exemplary schemes it may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example, size exclusion or ion exchange chromatography, high, medium, or low pressure liquid chromatography, small scale and preparative thin or thick layer chromatography, as well as techniques of small scale thin layer and flash chromatography.

Another class of separation methods involves treatment of a mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like.

Selection of appropriate methods of separation depends on the nature of the materials involved. For example, boiling point, and molecular weight in distillation and sublimation, presence or absence of polar functional groups in chromatography, stability of materials in acidic and basic media in multiphase extraction, and the like. One skilled in the art will apply techniques most likely to achieve the desired separation.

EXAMPLES

Example 1

4-2'-Deoxy-β-D-ribofuranosyl)-2-amino-3,6-dimethylpyridine

A mixture of palladium (II) acetate (0.029 g, 0.13 mmol), triphenylarsine (0.079 g, 0.26 mmol) and $CH_3CN$ (8 mL) was stirred under an Argon atmosphere at room temperature. A solution of 1,4-anhydro-2-deoxy-3-[(1,1-dimethylethyl) diphenylsilyl]-D-erythro-pent-1-en-itol (0.513 g, 1.45 mmol) and tributylamine (0.405 mL, 1.7 mmol) in $CH_3CN$ (8 mL) was added followed immediately by addition of 2-amino-3,6-dimethyl-4-iodopyridine (0.322 g, 1.3 mmol). The mixture was stirred at 60° C. for 15 h and then cooled to 0° C. Added was acetic acid (0.245 mL, 4.3 mmol) and 1.0 M tetrabutylammonium fluoride in tetrahydrofuran (2.2 mL, 2.2 mmol). The mixture was stirred for 30 min., evaporated, triturated with 1:10 mixture of $CHCl_2$/ether (50 mL), and stored at −20° C. for 30 min. After removal of the filtrate, the solid was dissolved into a 1/1 mixture of $CH_3CN$/acetic acid (26 mL) and cooled to 0° C. Triacetoxyborohydride (0.367 g, 1.74 mmol) was added and the mixture stirred for 30 min., evaporated, and evaporated twice from toluene. Silica gel chromatography 10–15% $CH_3OH$ (1% conc. $NH_4OH$)/$CH_2Cl_2$ yielded 0.212 g (0.89 mmol, 61%) of product.

Example 2

3,6-Dimethyl-5-iodo-2-Pyridone

2-Amino-3,6-dimethyl-5-iodopyridine (4.01 g, 16.2 mmol) was dissolved in 0.5 M $H_2SO_4$ (70 mL) and the resulting solution cooled to 0° C. with stirring. A solution of sodium nitrite (3.3 g, 48.0 mmol) in $H_2O$ (5 mL) was added dropwise over 10 min. at 0° C. with vigorous stirring. After 1.5 h the cooling bath was removed and the mixture warmed to r.t. over 1 h. The solid was vacuum filtered, washed with $H_2O$ (50 mL), the solids air dried and then dried under vacuum for 18 h, yielding 3.9 g (15.7 mmol, 97%) of white solid.

Example 3

6-Amino-2,5-Lutidine

6-Amino-2,5-lutidine (aminolutidine) was prepared by the method of Rao, K. V.; Venkateswarlu, P.; *J. Heterocyclic Chem.* (1975) 12:731–735, in particular page 732, column 2, paragraph 2, titled "6-amino-2,5-lutidine."

Example 4

2-amino-3,6-dimethyl-5-iodo Pyridine 7.0 g (38.5 mmole) of aminolutidine acetate was dissolved into $H_2O$ (100 mL) and solid NaOH was added until the pH of the solution was >10. 20g of NaCl was dissolved into this solution and the aminolutidine was extracted into $CH_2Cl_2$ (2×100 mL), dried over $Na_2SO_4$ and evaporated to an oil. To this oil was added $CH_2Cl_2$/$Et_2O$ (80 mL, 1/1), the mixture cooled to ~5° C. and 6.5 g (40 mmole) of ICl in $CH_2Cl_2$ (40 mL) was added dropwise over 10 min. After addition was complete $Et_2O$ (40 mL) was added and the mixture removed from the ice-bath After stirring for 1 hr. $Et_2O$ (40 mL) was added, the solid filtered, washed with $Et_2O$ and the supernatant evaporated. The product was dissolved into 1N HCl, washed with $CH_2Cl_2$, the aqueous phase made basic with solid NaOH and the product isolated by filtration. Yield 3.2 g (13 mmole, 68%).

Example 5

1,4-Anhydro-2-deoxy-3-O-[(1,1-dimethylethyl) diphenylsilyl]-D-erythro-pent-1-enitol 1,4-Anhydro-2-deoxy-3[(1,1-dimethylethyl) diphenylsilyl]-D-erythro-pent-1-enitol was prepared by the method of Farr, R. N.; Daves, G. D., Jr.; *J. Carbohydrate Chem.* (1990) 9(5):653–660, in particular, page 658, paragraph 1, titled "1,4-Anhydro-2-deoxy-3O-[(1,1-dimethylethyl)diphenylsilyl]-D-erythro-pent-1-enitol."

Example 6

4-(2'-Deoxy-β-D-ribofuranosyl)-3,6-dimethyl-2-pyridone

A. A mixture of palladium (II) acetate (0.200 g, 0.89 mmol), triphenylarsine (0.542 g, 1.77 mmol) and $CH_3CN$ (20 mL) was stirred under an Argon atmosphere at room temperature. A solution of 1,4-anhydro-2-deoxy-3O-[(1,1-dimethylethyl)diphenylsilyl]-D-erythro-pent-1-enitol (3.13 g, 8.83 mmol) and tributylamine (3.16 mL, 13.2 mmol) in $CH_3CN$ (30 mL) was added under an Argon atmosphere followed by addition of solid 3,6-dimethyl-5-iodo-2-pyridone (2.2 g, 8.83 mmol). The mixture was stirred at 60° C. for 18 h and then evaporated. Silica gel chromatography (5–7.5% $CH_3OH/CH_2Cl_2$) yielded 1.30 g (2.74 mmol, 31%) of solid.

B. The solid of Example 6A was dissolved in THF (40 mL) and cooled to 0° C. Acetic acid (0.19 mL) was added followed by 1 M tetrabutylammonium fluoride (3.0 mL, 3.0 mmol). The mixture was stirred for 30 min., evaporated, triturated with ether (60 mL) and the filtrate removed. The solid was dissolved in 1/1 $CH_3CN$/acetic acid (40 mL) and cooled to 0° C. Triacetoxyborohydride (0.876 g, 4.1 mmol) was added and the mixture stirred for 1 h at 0° C., evaporated and silica gel chromatography (10–12% $CH_3OH/CH_2Cl_2$) yielded 0.600 g (2.51 mmol, 92%) of product.

Example 7

Footprint Analysis

DNase footprint analysis of a 370-bp restriction fragment containing the target sequence was preformed in the conventional manner (Froehler, B. C. and Ricca, D. J., *J. Am. Chem. Soc.* (1992) 114:8320–8322; Cooney, M.; Czemuszewicz, G.; Postel, E. H.; Flint, S. J.; Hogan, M. E., *Science* (1988) 241:456–459; Francois, J. C.; Saison-Benmoaras, T.; Helene, C; *Nucleic Acids Res.* (1988) 16:11431–11440; Matteucci, M.; Lin, K.-Y.; Butcher, S.; Moulds, C.; *J. Am. Chem. Soc.* (1991) 113:7767–7768). The results are shown below in Table 10. The triple-helix formation was assessed via footprint assay for the analog targeted to both Select I (SEQ ID NO: 1 5'TCTCCCTCTCTTTTT3') and Select II (SEQ ID NO: 2 5'TCTCTCTCTCTTTTT3') cassettes vs. the T/5meC Control (5 meC is 5-methyl C). The results are at least 10-fold enhancement in binding at pH=7.2. Specificity of binding was maintained.

TABLE 10

| Sequence | Cas I ($\mu$M) | | | Cas II ($\mu$M) | | |
|---|---|---|---|---|---|---|
| | 10 | 1 | 0.1 | 10 | 1 | 0.1 |
| SEQ ID NO:3 5'TCTCTCTCTCTTTTT3' | – | – | – | + | + | – |
| SEQ ID NO:4 5'TPTPTPTPTPTTTTT3' | – | – | – | + | + | + |
| SEQ ID NO:5 5'2$^P$P2$^P$P2$^P$P2$^P$P2$^P$P2$^P$P2$^P$2$^P$2$^P$2$^P$2$^P$3' | – | – | – | + | – | – |
| SEQ ID NO:6 5'TPTPPPTPTPTTTTT 3' | + | + | +/– | – | – | – |
| SEQ ID NO:7 3'TCTCTCTCTCTTTTT 5' | – | – | – | + | +/– | – |
| SEQ ID NO:8 3'2$^P$P2$^P$P2$^P$P2$^P$P2$^P$P2$^P$P2$^P$2$^P$2$^P$2$^P$2$^P$3' | – | – | – | – | – | – |

+= protection
–= no protection
+/–= partial protection
P= 2-aminopyridine
2$^P$= 2-pyridinone
C= 5-methyl dC
T= thymidine

| | Duplex Tm | | | |
|---|---|---|---|---|
| | RNA | | DNA | |
| ODN | Tm | ΔTm | Tm | ΔTm |
| Control | 61.5 | – | 52.5 | – |
| 2-aminopyridine | NT | – | NT | – |
| 2-pyridinone | 59.0 | –2.5 | 47.0 | –5.5 |

Control= SEQ ID NO:3 5'TCTCTCTCTCTTTTT3'
2-aminopyridine= SEQ ID NO:4 5'TPTPTPTPTPTTTTT3'
2-pyridinone= SEQ ID NO:9 5'TCTCTCTCTC2$^P$2$^P$2$^P$2$^P$2$^P$3'
NT= no transition All literature and patent citations above are hereby expressly incorporated by reference at the locations of their citation. Specifically cited sections or pages of the above cited works are incorporated by reference with specificity. The invention has been described in detail sufficient to allow one of ordinary skill in the art to make and use the subject matter of the following claims. It is apparent that certain modifications of the methods and compositions of the following claims can be made within the scope and spirit of the invention.

What is claimed is:

1. An oligonucleotide compound with internucleoside linkages that includes at least one nucleoside of the formula:

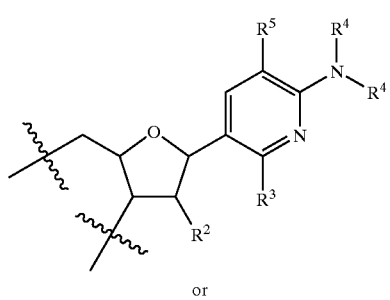

I or

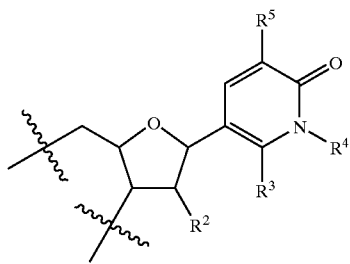

II wherein:

$R^2$ is H, F, —$OR^1$, or —$OR^6$;
  wherein $R^1$ is H or a hydroxy protecting group;

$R^3$ is H or —$CH_3$;

each $R^4$ formula I and II are independently H or an amine protecting group, or both $R^4$ groups of formula I are taken together to form a cyclic amine protecting group;

$R^5$ is H, —$CH_3$, or —C≡C—$CH_3$ and $R^6$ is

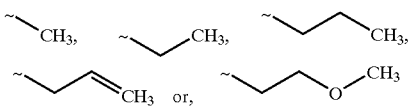

and salts, solvates, resolved enantiomers and purified diastereomers thereof.

2. The compound according to claim 1, wherein at least one of the internucleoside linkages is a phosphorothioate linkage.

* * * * *